US005437979A

United States Patent [19]

Rampal et al.

[11] Patent Number: 5,437,979
[45] Date of Patent: Aug. 1, 1995

[54] SOLID PHASE SYSTEM FOR SEQUENTIAL REACTIONS

[75] Inventors: Jang B. Rampal, Fremont; Jon F. Harbaugh, Los Altos, both of Calif.

[73] Assignee: Beckman Instruments, Inc., Fullerton, Calif.

[21] Appl. No.: 934,286

[22] Filed: Aug. 24, 1992

Related U.S. Application Data

[63] Continuation of Ser. No. 384,576, Jul. 24, 1989, abandoned.

[51] Int. Cl.6 ............... C12Q 1/68; C12M 1/36; G01N 35/00; G01N 35/02
[52] U.S. Cl. .................... 435/6; 435/289; 436/43; 436/50; 436/55
[58] Field of Search ............ 435/6, 289; 436/43, 436/50, 55

[56] References Cited

U.S. PATENT DOCUMENTS

| | | | |
|---|---|---|---|
| 2,423,173 | 7/1947 | Brady et al. | 222/189 |
| 4,155,711 | 5/1979 | Zelagin et al. | 436/500 |
| 4,426,451 | 1/1984 | Columbus | 436/518 |
| 4,483,825 | 11/1984 | Fatches | 422/100 |
| 4,592,994 | 6/1986 | Mattiasson | 435/7 |
| 4,623,629 | 11/1986 | Kerschensteiner | 436/518 |
| 4,774,058 | 9/1988 | Mehl | 422/101 |
| 5,057,426 | 10/1991 | Henco et al. | 435/270 |

FOREIGN PATENT DOCUMENTS

| | | |
|---|---|---|
| 3717210 | 12/1988 | Germany . |
| 3717211 | 12/1988 | Germany . |
| 57-35707 | 7/1982 | Japan . |

OTHER PUBLICATIONS

Krottinger et al, CA90(10): 80252e.
Alvarado-Urbina et al, Science, v. 214, Oct. 16, 1981, pp. 270-274.
BioFeedback-"Automated Column Equilibration, Washing, Sample Loading and Elution of Bench-Packed Mini-Columns"; 336 BioTechniques; vol. 12, No. 3 (1992).
R. K. Wilson et al., "Automation of Dideoxynucleotide DNA Sequencing Reactions Using A Robotic Workstation," Biotechniques, vol. 6, No. 8 (1988).
G. Alvarado-Urbina et al., "Automated Synthesis of Gene Fragments," Science, vol. 214, Oct. 16, 1981.
J. W. Giles et al., "An Economical System for Automated DNA Synthesis," 1987.
L. G. Bachas et al., "Binding Proteins as Reagents in Enzyme-Linked Competitive Binding Assays of Biological Molecules," BioTechniques, vol. 4, No. 1 (1986).
M. E. Schott, "A Simple Manual Method for Oligonucleotide Synthesis," Amer. Biotech. Lab., (1985).
J. Bremner et al., "Options for DNA Synthesis," Mar.-Apr. 1985. pp. 46-52 only.
R. T. Pon et al., "Derivatization of Controlled Pore Glass Beads for Solid Phase Oligonucleotide Synthesis," BioTechniques, vol. 6, No. 8 (1988).

Primary Examiner—Mindy B. Fleisher
Attorney, Agent, or Firm—William H. May; Paul R. Harder; Janis C. Henry

[57] ABSTRACT

Procedures such as oligonucleotide, peptide or protein syntheses or sequencing, or immunological or other biospecific assays involving long sequential series of chemical reactions are performed on a solid phase support retained in a pipette tip. The manipulations involved in bringing the solid support into contact with the various reagents or reactants involved in the procedure are performed and controlled by automated instrumentation.

7 Claims, 1 Drawing Sheet

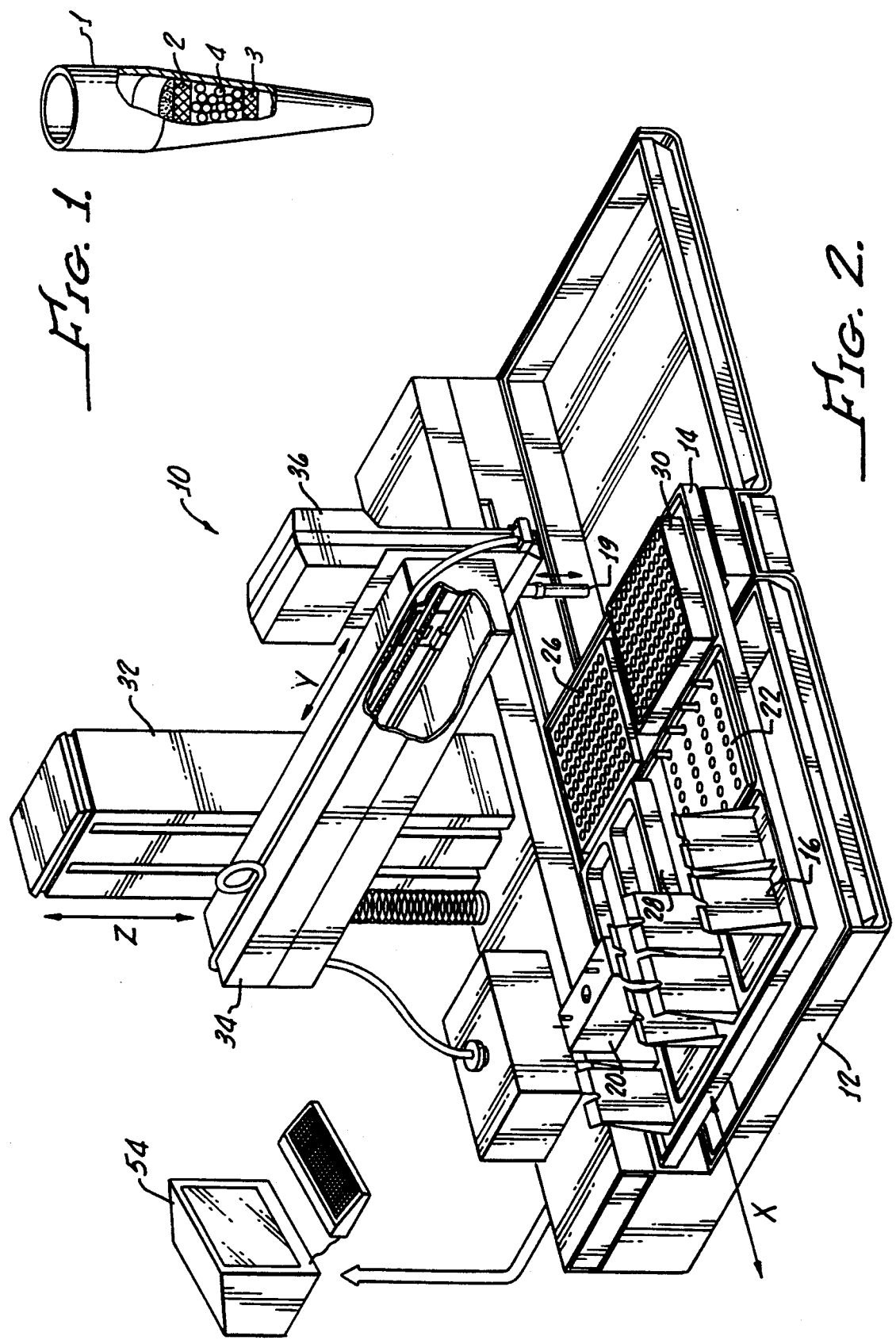

SOLID PHASE SYSTEM FOR SEQUENTIAL REACTIONS

This is a continuation of application Ser. No. 07/384,576, filed Jul. 24, 1989 now abandoned.

This invention relates to reaction systems for use in biochemical procedures, and in particular to reactions or protocols performed in sequential series, all involving species immobilized on a solid support.

BACKGROUND OF THE INVENTION

Biochemical procedures involving sequential reactions, such as for example, oligonucleotide synthesis, oligonucleotide sequencing reactions, peptide and polypeptide synthesis, and sequential binding assays, have spawned a body of technology aimed at automating the procedures. The purpose of these developments has been to reduce the time required to perform the sequences, as well as to achieve uniformity in the manner in which the sequences are performed, thereby permitting large numbers of sequences to be performed simultaneously and eliminating the potential for human error.

Sequential reactions of this type are commonly performed by immobilizing a species on a solid phase support and bringing the immobilized species in contact with a series of liquid solutions containing the reagents or reactants needed to perform the reactions. The prior art includes a variety of system configurations for achieving this, whereby the solid phase is retained in receptacles such as wells or columns and the movement of liquids into and out of contact with the solid phase is achieved by automated valves or syringes.

SUMMARY OF THE INVENTION

What has now been developed is a novel method and system for performing such reaction sequences, whereby the solid phase is retained in a pipette tip in an automated pipetting apparatus, or any similar reaction vessel, such that all reactions occur inside the pipette tip itself. This avoids the need to secure the solid phase to an immovable object or to decant or filter the solid phase in between reactions. It also minimizes exposure of the solid phase to the surroundings by retaining the solid phase in an almost fully enclosed environment, thereby enhancing reliability, reproducibility and safety. The use of an automated apparatus readily permits changes in the reagents used and in the timing intervals and sequence of reactions, thereby enhancing the flexibility of the system.

BRIEF DESCRIPTION OF THE DRAWINGS

FIG. 1 is a perspective view of a pipette tip partially broken away to show the solid phase support retained therein in accordance with one embodiment of the present invention.

FIG. 2 is a perspective view of the Biomek 1000 automated laboratory workstation implemented with the pipette tip in accordance with the present invention.

DETAILED DESCRIPTION OF THE INVENTION AND PREFERRED EMBODIMENTS

The pipette tip used to house the solid support may be any such piece of equipment which is capable of or adaptable for use with an automated apparatus of the type described herein. The pipette tip will be selected on the basis of its volumetric capacity to be sufficient to accommodate the desired quantity of solid phase support. On this basis, the actual volume is not critical, and a wide range may be used. In most applications, however, the most practical pipette tips will be those having an internal volume ranging from about 50 $\mu L$ to about 5000 $\mu L$. As an example, a standard 1000 $\mu L$ pipette tip will be useful in many applications.

For use in the present invention, the pipette tip will be modified or adapted to hold the solid phase support in a secure manner while still permitting the free flow of fluids into and out of the pipette tip. This may be achieved in any conventional manner. As one example, referring to FIG. 1, porous frits 2 and 3 of an inert material such as glass or plastic may be secured inside the pipette tip 1 by a friction fit, one above and one below the solid phase support 4. In some cases, a single frit supporting the solid phase support from below will suffice.

The automated apparatus to which the pipette tip is mounted may be any of the variety of equipment commercially available for sequential operations involving liquid transfers to and from receptacles such as standard 96-well plates or modified reservoirs of various types. Typical examples of such equipment are computer-controlled bench-top systems designed for the performance and analysis of enzyme-linked immunoassays and other biospecific assay protocols, as well as those described in the literature for use in oligonucleotide synthesis and sequencing reactions. One example in particular is the Biomek 1000 automated laboratory workstation, obtainable from Beckman Instruments, Inc., Palo Alto, Calif., and the P1000 pipette tool designed for use with the Biomek 1000. In general, single or multiple channel pipette tools may be used, as well as other accessories manufactured and available for use in conjunction with the instrument, such as appropriate liquid reagent receptacles (96-well culture plates, for example), biological containment hoods, power connections, and the like.

Programming of the apparatus is likewise achieved in the conventional manner, typically by the use of desktop computers such as the IBM PC/AT or equivalent equipment. The program may be prearranged or set up by the operator on an individual basis for a specific reaction sequence, and will consist of a series of pipetting, dispensing and pause functions in accordance with the sequence.

The solid phase support may be any water-insoluble macroscopic solid material on which the first reactant or chemical species involved in the reaction sequence can be immobilized. The method of immobilization may be any method by which the species is securely fixed to the support and yet capable of dissociation upon completion of the reaction sequence. Preferred methods of immobilization are covalent bonds, and preferred solid supports are accordingly those which have surface functional groups readily susceptible to the formation of covalent bonds with the chemical species, or those which are readily activated or derivatized by the attachment of such functional groups. With these considerations in mind, any of the wide range of conventional materials used in the biotechnology art as solid supports may be used. Examples are silica glass, controlled pore glass (CPG), polystyrene, and Sepharose (agarose).

The form of the solid phase support may also vary. Any form which will provide ample surface area accessible to liquids flowing through and indeed permit the flow of the liquids to achieve full contact may be used. Examples of usable forms are gels, particles and beads.

The amount of solid phase support is not critical, and will vary according to the needs of the particular reaction sequence, procedure or protocol to be performed, or the product to be formed. For most applications, amounts ranging from about 1 mg to about 100 mg will provide the best results.

The types of procedures or protocols to which the present invention is applicable include any repetitive or sequential chemical process which involves a large number of steps. Examples include DNA and RNA syntheses, DNA and RNA degradations (for sequencing purposes), peptide syntheses and degradations, protein syntheses and degradations, and analytical procedures such as biospecific or immunological assays. The reaction sequences may therefore involve stepwise construction of linear chains, such as in oligonucleotide and peptide syntheses, beginning with the chemical species bonded to the solid support, or sequential treatments of the bound chemical species with a succession of reagents, such as in certain types of assays, or a combination of the two. Such techniques are well known in the art.

The reagents or reactants present in liquid solution for contact with the species immobilized on the solid support will likewise vary depending on the procedure being performed. These may include, for example, immunological or biospecific binding members, enzyme substrates or other detection species or mechanisms, nucleotide monomers, and blocking or deblocking agents.

Once the sequence of reactions is complete, the species bound to the solid support is a finished product, which may be a linear chain if the procedure involved synthesis of a oligonucleotide, protein or peptide, or the final form of an analyte after all treatments required for the assay have been performed, if the procedure involved an assay. Removal of the bound species from the solid support may be achieved by conventional means of dissociation well known among those skilled in the art. Synthesized oligonucleotides, for example, may be removed by treatment with concentrated ammonium hydroxide. In other types of procedures, changes in pH may be used to remove the product. The most appropriate means in each case will of course vary with the type of procedure having been performed and the method by which the initial species was bound to the support, whether it be nucleoside, protein, peptide or analyte.

The foregoing is offered primarily for purposes of illustration. Numerous variations, modifications and further alternatives well known among those skilled in the art may be made without departing from the spirit and scope of the invention.

What is claimed is:

1. A method for performing a sequential series of reactions on a chemical species, said method comprising:
   (a) immobilizing said chemical species on a solid support retained in a pipette tip mounted on an automated apparatus which is programmable to draw reactants into said pipette tip from receptacles at preselected locations and to expel reactants from said pipette tip in accordance with a preselected time sequence;
   (b) placing said reactants in liquid form in said receptacles; and
   (c) causing said apparatus to draw said reagents into said pipette tip in accordance with a preselected sequence to contact said chemical species so immobilized, thereby causing said sequential series of reactions to occur.

2. A method in accordance with claim 1 in which said reactants are nucleosides, and said sequential series of reactions are sequential coupling reactions to form an oligonucleotide.

3. A method in accordance with claim 1 in which said reactants are amino acids, and said sequential series of reactions are sequential coupling reactions to form a peptide or protein.

4. A method in accordance with claim 1 in which said reactants are biospecific binding members, and said sequential series of reactions collectively comprise a biospecific binding assay.

5. A method in accordance with claim 1 in which said solid support is selected from the group consisting of polystyrene and silica.

6. A method for automatically performing a sequential series of reactions on a chemical species using an automated laboratory workstation operating on a pipette, comprising the steps of:
   configuring a pipette tip on the pipette, said pipette tip retaining a solid phase support therein, said solid phase support being of a material capable of immobilizing a chemical species;
   configuring receptacles on the automated laboratory workstation containing different reagents required for a desired sequence of reactions;
   programming the automated laboratory workstation to aspirate reagents into and dispense reagents from the pipette tip in sequence to cause the immobilized chemical species to react with the reagents in the pipette tip in accordance with the desired sequence of reactions.

7. A method in accordance with claim 1 further including drawing a reagent into said pipette tip which has the characteristic of reacting with and separating said chemical species which has been subject to said sequential series of reactions from said solid support.

* * * * *